United States Patent [19]

Yamaguchi et al.

[11] 4,319,489
[45] Mar. 16, 1982

[54] ULTRASONIC DIAGNOSTIC METHOD AND APPARATUS

[75] Inventors: Keiki Yamaguchi; Yasuhito Takeuchi; Toru Shimazaki; Naoki Seki, all of Musashino, Japan

[73] Assignee: Yokogawa Electric Works, Ltd., Tokyo, Japan

[21] Appl. No.: 135,157

[22] Filed: Mar. 28, 1980

[51] Int. Cl.³ .............................................. G01N 29/00
[52] U.S. Cl. ........................................ 73/626; 128/660
[58] Field of Search .............................. 128/660–663; 73/625–626

[56] References Cited

U.S. PATENT DOCUMENTS

| | | | |
|---|---|---|---|
| 4,070,905 | 1/1978 | Kossoff | 128/660 |
| 4,075,598 | 2/1978 | Takamizawa et al. | 73/626 |
| 4,136,325 | 1/1979 | Takamizawa et al. | 73/626 |
| 4,159,462 | 6/1979 | Rocha et al. | 128/661 |
| 4,161,122 | 7/1979 | Buchner | 128/660 |
| 4,211,949 | 7/1980 | Brisken et al. | 128/660 |
| 4,217,516 | 8/1980 | Iinuma et al. | 128/660 |

*Primary Examiner*—Robert W. Michell
*Assistant Examiner*—Francis J. Jaworski
*Attorney, Agent, or Firm*—Parmelee, Johnson, Bollinger & Bramblett

[57] ABSTRACT

An ultrasonic diagnostic method and apparatus are provided for probing the condition in a tissue of a living body by projecting an ultrasonic beam onto the living body from a vibrator array transducer probe consisting of a plurality of tiny ultrasonic vibrators. The apparatus executes two scanning actions, of which one is a normal linear scanning that drives the ultrasonic vibrators sequentially in the manner to cause a sequential parallel shift of the ultrasonic beam substantially perpendicular to the vibrator array, and the other of which is an inclined linear scanning that drives the ultrasonic vibrators at individually different timings while sequentially shifting the driven vibrators in the manner to cause sequential parallel shift of the ultrasonic beam having an angle of inclination against the vibrator array. The images obtained through the normal linear scanning and the inclined linear scanning are combined to form a composite high-resolution image.

7 Claims, 9 Drawing Figures

ULTRASONIC DIAGNOSTIC METHOD AND APPARATUS

BACKGROUND OF THE INVENTION

1. Field of the Invention

The present invention relates to an ultrasonic diagnostic method and apparatus, and more particularly to such a method and apparatus which is capable of producing a sectional image of a living body by projecting an ultrasonic beam onto the living body and receiving an echo reflected from the interface between heterogeneous constituents whose acoustic impedances are different from each other.

2. Description of the Prior Art

In conventional equipment of the type known heretofore, the scanning of an ultrasonic beam is performed by either a linear scanning system or a sector scanning system.

The linear scanning is carried out as illustrated in FIG. 1 by the use of a vibrator array 10 consisting of a plurality of vibrators, wherein the vibrators are driven sequentially in such a manner that some (e.g. three) of them grouped as $a_1$-$a_2$-$a_3$, $a_2$-$a_3$-$a_4$, etc. are excited in such groups to cause a sequential parallel shift of an ultrasonic beam which is substantially perpendicular to the vibrator array 10. The reason for grouping three vibrators for each excitation is to improve the directivity of the ultrasonic beam.

Sector scanning is carried out as illustrated in FIG. 2, wherein the entire array of vibrators 10 are driven at individually different timings such that the ultrasonic beam as a whole is turned to a certain direction, which is then changed sequentially to deflect the ultrasonic beam in the shape of a sector.

The linear scanning system is disadvantageous in that the range (visual field) of the image obtained is limited to the width L of the vibrator array 10. Consequently, in order to widen the visual field, the number of vibrators must be increased to widen the array 10 increasing the complexity of the system. Moreover, another disadvantage is the deteriorating degree of intimate contact with the wall of the living body. As for the sector scanning system, it also has some disadvantages including a narrow visual field at a short distance and an unsatisfactory resolution for long-distance images.

SUMMARY OF THE INVENTION

It is an object of the present invention to provide an ultrasonic diagnostic method and apparatus which is capable of producing high-resolution sectional images.

Another object of this invention is to provide an improved ultrasonic diagnostic method and apparatus wherein the range (visual field) of an image is greater than the width of a vibrator array.

In carrying out this invention in one illustrative embodiment thereof, an ultrasonic beam emitted by a vibrator array is scanned in at least two different ways over a target being examined including a normal linear scan and an inclined linear scan which causes a sequential parallel shift of the ultrasonic beam having an angle of inclination against the vibrator array. The plural images obtained through such scanning actions are combined to form a composite image.

BRIEF DESCRIPTION OF THE DRAWINGS

The invention, together with further objects, aspects, features and advantages thereof, will be better understood from the following description taken in conjunction with the accompanying drawings.

DESCRIPTION OF THE PREFERRED EMBODIMENTS

Figure 1:
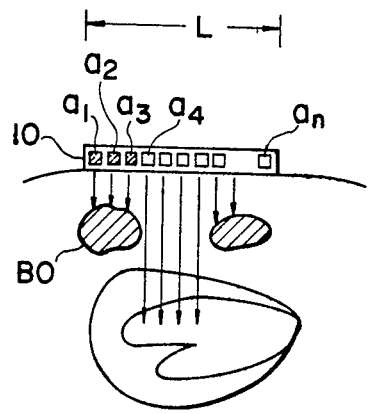
FIG. 1 illustrates a conventional linear scanning system.
Figure 2:
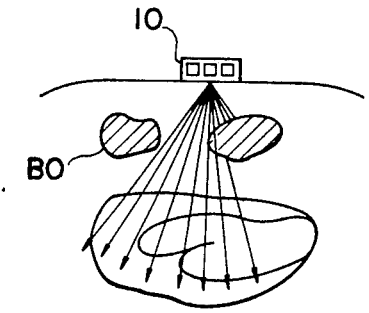
FIG. 2 illustrates a conventional sector scanning system.
Figure 3:
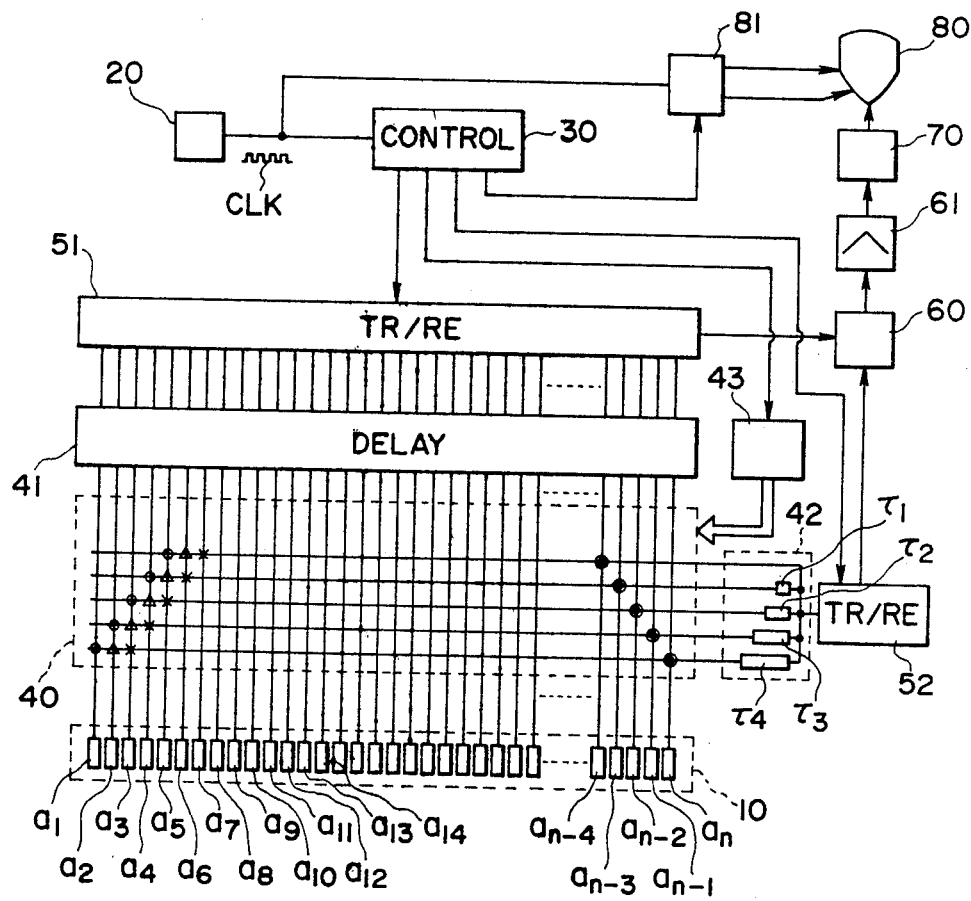
FIG. 3 is a block diagram of an ultrasonic diagnostic equipment embodying the present invention.

In the block diagram of FIG. 3 showing an embodiment of this invention, a vibrator array 10 comprises a multiplicity of tiny ultrasonic vibrators $a_1, a_2, a_3 \ldots a_n$ arranged in a linear array. A clock pulse generator 20 produces output clock pulses CLK of a fixed period which are used for controlling the equipment, and these pulses are applied to a control circuit 30. A transmitter-receiver assembly 51 which is provided for the execution of normal linear scanning includes a multiplicity of transmitters-receivers and scanners which are connected to vibrators $a_1$-$a_n$ respectively via a first delay network 41. Another transmitter-receiver assembly 52 provided for the execution of inclined linear scanning is connected to some of the vibrators $a_1$-$a_n$ via a second delay network 42 and a matrix switch circuit 40. The second delay network 42 consists of a plurality of delay circuits $\tau_1, \tau_2, \tau_3$, etc. whose delay times are individually different from one another, so that signals are fed therefrom at individually different timings to horizontal leadwires of the matrix switch circuit 40. This switch circuit 40 includes a plurality of vertical leadwires connected to the vibrators $a_1$-$a_n$ respectively, and a plurality (in this example, five) horizontal leadwires connected to the delay network 42 and switches to connect each crossing point (intersection) of the vertical leadwires and horizontal leadwires. During the inclined linear scanning, the intersections of the vertical and horizontal leadwires are connected sequentially by the control signals from the switch control circuit 43 in the order illustrated by marks o, ∆ and x.

During normal linear scanning, an image composition circuit 60 feeds the output signal of the first delay network 41 to an amplifier 61 via the transmitter-receiver assembly 51. During the inclined linear scanning, the circuit 60 feeds the output signal of the second delay network 42 to the amplifier 61 via the transmitter-receiver assembly 52. The output of the amplifier 61 is applied to a B-mode intensity modulation signal generator 70, which then applies its intensity modulation signal to a display device 80 such as cathode-ray tube. A scanning circuit 81 receives both the clock pulses CLK and the control signal from the control circuit 30, and feeds a deflection signal to the cathode-ray tube 80.

Figure 4:
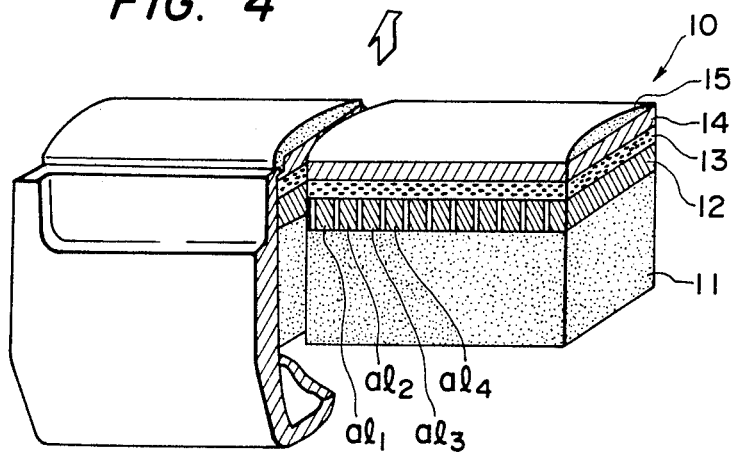
FIG. 4 is a perspective view of an exemplary vibrator array (probe) employed in the equipment of FIG. 3.

FIG. 4 is a perspective view of an exemplary vibrator array 10 (probe) employed in the equipment of FIG. 3. The vibrator array 10 comprises a piezoelectric vibratory plate 12 bonded onto a backing member 11 composed of ferrite rubber or the like, which is cut by means of a dicing saw to produce a multiplicity of independent tiny ultrasonic vibrators a11, a12, a13, etc. as illustrated in FIG. 4. For the purpose of enhancing the ultrasonic-beam generation efficiency and the reception sensitivity as well as for matching the impedance to the body of a patient, the surface of each vibrator is covered with a laminated glass layer 13, a high polymer film 14 and a lens 15 composed of silicone rubber. The directivity of the ultrasonic beam is further improved by connecting a plurality (e.g. three) of ultrasonic vibrators a11, a12, and a13 electrically to one another so that these serve as a single vibrator $a_1$ ($a_2$ ... ) of FIG. 3.

Hereinafter the operation of the equipment having the above-mentioned configuration will be described with reference to FIGS. 5 through 8.

Figure 5:
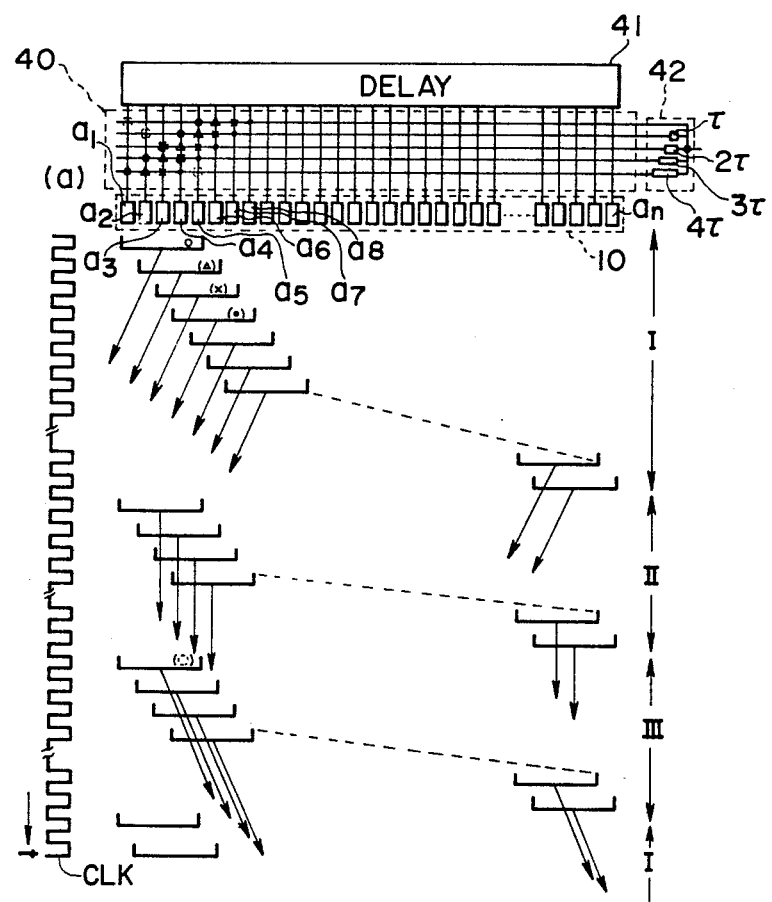
FIG. 5 illustrates the manner in which the ultrasonic vibrators are driven.
Figure 6:
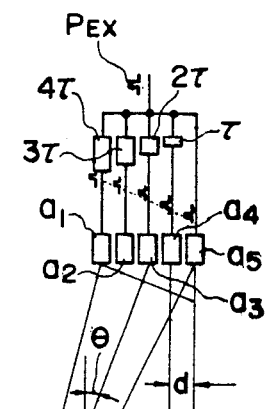
FIG. 6 illustrates how a leftward-inclined scanning is executed.

The clock pulse generator 20 produces clock pulses of a fixed period as shown in FIG. 5(a), where the time base thereof is in the vertical direction. The period of the clock pulses is determined in relation to the diagnosis distance. The control circuit 30 feeds its control signals to the switch control circuit 43, which then connects the intersections of the vertical and horizontal leadwires first as marked with o in the matrix switch circuit 40. As a result of such connection, the exciting pulses $P_{EX}$ from the transmitter-receiver assembly 52 are fed to the ultrasonic vibrators $a_1$-$a_5$ in the manner that, as shown in FIG. 6, the pulse to the vibrator $a_5$ is applied directly without any delay, while the pulses to the vibrators $a_4$, $a_3$, $a_2$ and $a_1$ are applied with delays $\tau$, $2\tau$, $3\tau$ and $4\tau$, respectively. Since the ultrasonic vibrators $a_1$, $a_2$, $a_3$ ... $a_n$ are arranged at a pitch d to constitute the vibrator array 10, when the exciting pulses are applied thereto at individually different timings in sequence with a delay increment of $\tau$, the center of the ultrasonic beams emitted from the vibrators $a_1$-$a_5$ have a directivity which is inclined leftward by $\theta = \sin^{-1}(C\cdot\tau/d)$ against the vibrator array 10 as illustrated in FIG. 6. In this equation, $\theta$ is the angle (hereinafter referred to as inclination angle) formed by the center of the ultrasonic beam and the line perpendicular to the vibrator array 10, and C is the propagation velocity of the ultrasonic beam in the medium.

Next, the switch control circuit 43 connects the intersections of the vertical and horizontal leadwires as marked with Δ in the matrix switch circuit 40. Upon this connection, exciting pulses are fed to the ultrasonic vibrators $a_2$-$a_6$ such that the pulse to the vibrator $a_6$ is applied directly without any delay, while the pulses to the vibrators $a_5$, $a_4$, $a_3$ and $a_2$ are applied with delays $\tau$, $2\tau$, $3\tau$ and $4\tau$, respectively. Therefore, the ultrasonic beam emitted from the vibrators $a_2$-$a_6$ is shifted in parallel slightly toward the right while maintaining the inclination angle $\theta$.

Subsequently, the switch control circuit 43 connects the intersections of the vertical and horizontal leadwires as marked with x, and so forth in the matrix switch circuit 40 for sequentially shifting the connected ultrasonic vibrators one by one to the right until such control is completed with respect to the vibrators $a_1$-$a_n$. Thus, it becomes possible to execute leftward-inclined linear scanning which causes sequential parallel shift of the ultrasonic beam inclined leftward against the vibrator array 10, as shown in FIG. 5-I. Although the inclination angle $\theta$ of the ultrasonic beam is changeable by varying the delay time $\tau$, it is effective to set the angle $\theta$ greater than 10 degrees in view of picking up the image on the reverse side of an object.

The ultrasonic beam emitted from the individual ultrasonic vibrators is reflected at the interface between two tissues, and the pulses reflected therefrom are received again by the ultrasonic vibrators. The pulses thus received are applied to the amplifier 61 by way of the matrix switch circuit 40, the delay network 42, the transmitter-receiver assembly 52 and the image composition circuit 60. And the amplified pulses are then applied to the B-mode intensity modulation signal generator 70. The amplifier 61 may be of logarithmic type such that the gain of the reflected signal at a long distance from the ultrasonic vibrator is large while the gain of the reflected signal at a short distance therefrom is amplified to a lesser degree. The sweep circuit 81 generates a signal corresponding to the diagnosis distance per period of the clock pulses and also a signal corresponding to the center position of the ultrasonic beam emitted from each ultrasonic vibrator. The cathode-ray tube 80 receives the output of the B-mode intensity modulation signal generator 70 as intensity modulation data and also the output of the scanning circuit 81 as a deflection signal, and performs B-mode display on its screen. Such leftward-inclined linear scanning provides a visual field illustrated in FIG. 7-I, where the ultrasonic beams are shown by solid lines. And during this scanning time, the action of the transmitter-receiver assembly 51 is kept at a stop.

In the next operational stage, the control circuit 30 disconnects the vertical and horizontal leadwires from each other in the matrix switch circuit 40 and, as illustrated in FIG. 5-II, the entire ultrasonic vibrators $a_1$-$a_n$ are driven sequentially by the transmitter-receiver assembly 51 while being shifted one by one such that five vibrators grouped as $a_1$-$a_5$, $a_2$-$a_6$, $a_3$-$a_7$ and so forth are excited at the same timing, thereby effecting linear scanning of the ultrasonic beams. The linear scanning thus executed is based on the prior art that causes a sequential parallel shift of the ultrasonic beam which is substantially perpendicular to the vibrator array 10. In this linear scanning, the signal received from each ultrasonic vibrator is applied to the amplifier 61 via the delay network 41 serving as a focusing circuit, the transmitter-receiver assembly 51 and the image composition circuit 60. The amplified signal from amplifier 61 is applied to the signal generator 70, whose intensity modulation signal is then displayed on the screen of the cathode-ray tube 80. The linear scanning described above provides a visual field of FIG. 7-II, where the ultrasonic beams are shown by broken lines.

Subsequently, the control circuit 30 feeds a control signal to the switch control circuit 43 to connect the intersections of the vertical and horizontal leadwires as marked with ⊙ in FIG. 5 in the matrix switch circuit 40. Upon such connection, exciting pulses are fed from the transmitter-receiver assembly 52 to the ultrasonic vibrators $a_1$-$a_5$ as shown in FIG. 8, where the pulse to the vibrator $a_1$ is applied directly without any delay while the pulses to the vibrators $a_2$, $a_3$, $a_4$ and $a_5$ are applied with delays $\tau$, $2\tau$, $3\tau$ an $4\tau$, respectively. When the exiting pulses are applied to the ultrasonic vibrators $a_1$-$a_5$ at individually different timings in sequence with a delay increment of $\tau$ as just mentioned, the center of the ultrasonic beams emitted from the vibrators $a_1$-$a_5$ have a directivity that is inclined rightward by $\theta = \sin^{-1}$ (C·τ/d) against the vibrator array 10 as illustrated in FIG. 8. Subsequently, the delay network 42 is so energized that, as shown in FIG. 5-III, the ultrasonic vibrators to be connected in the matrix switch circuit 40 are grouped as $a_2$-$a_6$, $a_3$-$a_7$, $a_4$-$a_8$ and so forth under control while being shifted one by one, and some (in this example, five) vibrators are driven at a timing different from the preceding five with a delay increment of τ. Thus, a rightward-inclined linear scanning is executed that causes sequential parallel shift of the ultrasonic beam inclined rightward against the vibrator array 10. Such rightward-inclined linear scanning provides a visual field of FIG. 7-III, where the ultrasonic beams are shown by one-dot chain lines.

In the following stage of the operation, the aforementioned leftward-inclined linear scanning, normal linear scanning and rightward-inclined linear scanning are executed in sequence repeatedly. As for the scanning order, the normal linear scanning may be followed by the leftward-inclined linear scanning and the rightward-inclined linear scanning. It is also possible to omit any one of the normal, leftward-inclined and rightward-inclined linear scanning actions.

Figure 7:
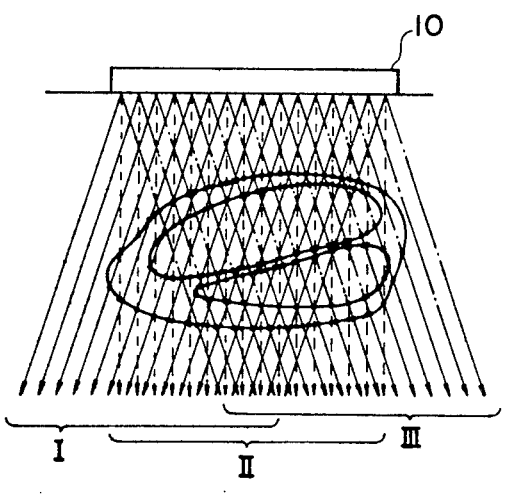
FIG. 7 shows the scanning state of an ultrasonic beam.
Figure 8:
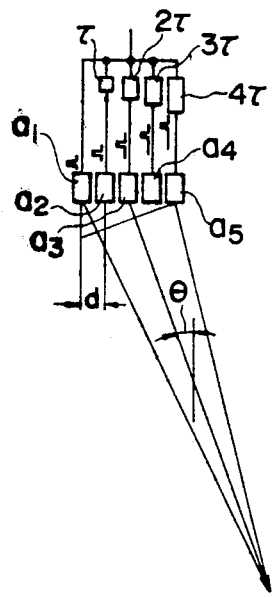
FIG. 8 illustrates how a rightward-inclined linear scanning is executed.

Due to such sequential repetition of the leftward-inclined linear scanning, normal linear scanning and rightward-inclined linear scanning, three images obtained through the individual scanning actions are displayed successively on the cathode-ray tube 80 as shown in FIG. 7. And by combining the three images with one another by utilizing the residual phosphorescence of the cathode-ray tube, scanning line density of the ultrasonic beam is increased to provide a composite B-mode image having a satisfactory resolution. In this case, the visual field is extendable in comparison with the known example where only the normal linear scanning is executed. Moreover, although it is difficult for the normal linear scanning alone to detect the presence of any interface which is parallel with the emitted ultrasonic beam, such an interface is detectable by the execution of the inclined linear scanning.

The B-mode images obtained through the individual scanning actions can be combined to form a composite image by utilizing the residual photoreceptive sense of eyes, a digital image memory or a scan converter in addition to residual phosphorescence on the screen of the cathode-ray tube. Such image composition is effected by addition, multiplication (addition of logarithms), maximum selection which takes the greatest absolute value, averaging or a combination thereof. The above description covers the case of combining the images obtained through the three actions of leftward-inclined linear scanning, normal linear scanning and rightward-inclined linear scanning. However, such image composition may be achieved also by successive execution of merely leftward-inclined and rightward-inclined linear scanning actions. It is also possible to form a composite image by combining the two images obtained through either the leftward or rightward-inclined scanning and the normal linear scanning.

Figure 9:
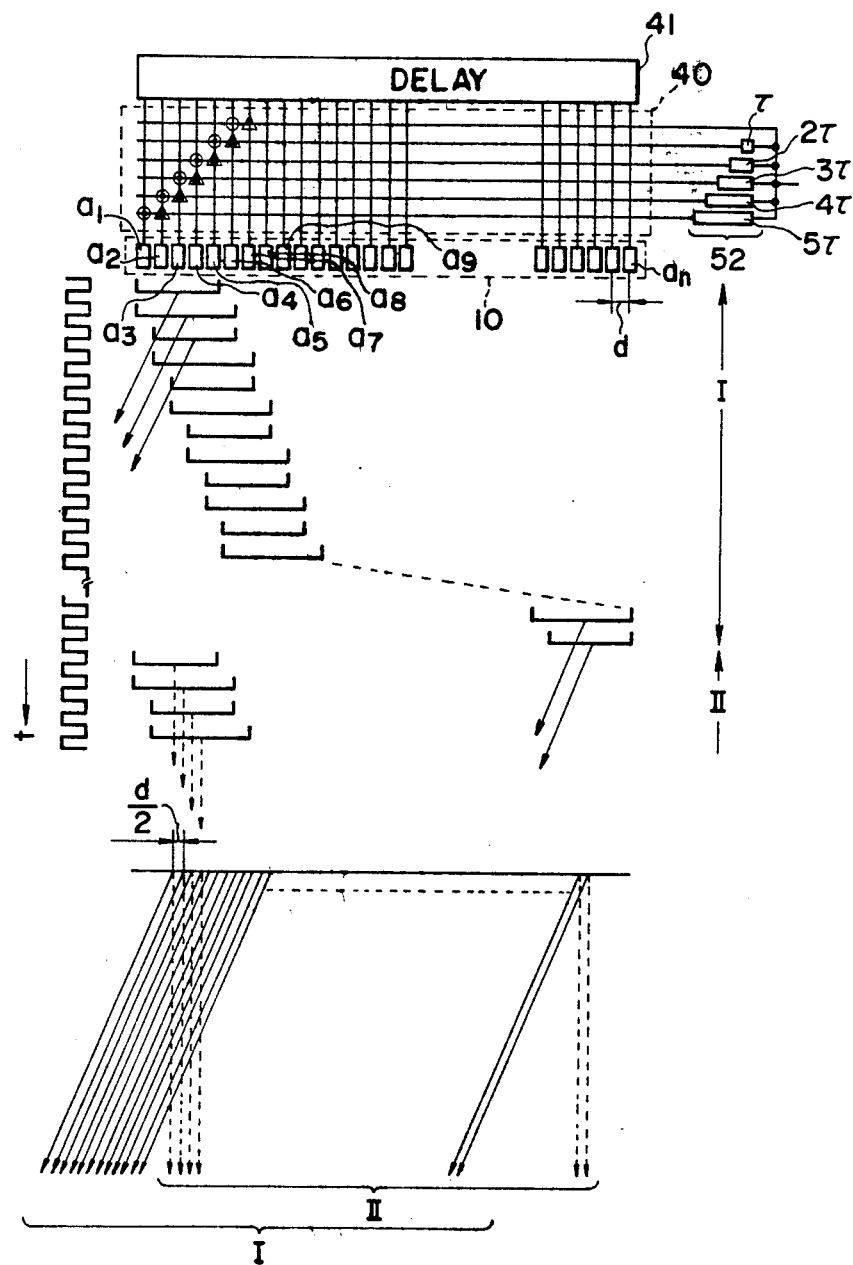
FIG. 9 shows another example of driving the ultrasonic vibrator in this invention.

FIG. 9 illustrates another example of driving the ultrasonic vibrators in the equipment of this invention. In this case, the leadwire connection in the matrix switch circuit 40 is selectively controlled in such a manner, that during the leftward-inclined linear scanning, the number of ultrasonic vibrators driven for simultaneous transmission and reception of beams with a delay τ from the preceding vibrators is changed one by one at a time to five, six, five, six and so forth to constitute groups of $a_1$-$a_5$, $a_1$-$a_6$, $a_2$-$a_6$, $a_2$-$a_7$... as shown in FIG. 9-I. That is, in the matrix switch circuit 40, the intersections of the vertical and horizontal leadwires are connected sequentially in the order of marks o, x and Δ. Also, during the normal linear scanning, the number of ultrasonic vibrators driven for simultaneous transmission and reception of beams is changed one by one at a time to five, six, five, six and so forth by the transmitter-receiver assembly 51 as shown in FIG. 9-II.

When the number of ultrasonic vibrators driven simultaneously is changed to m (=integer) and m+1 alternately, the center of the ultrasonic beams emitted therefrom is shifted at a rate of half the distance d between the adjacent ultrasonic vibrators. Therefore, as compared with the case of FIG. 5 where the number of ultrasonic vibrators driven simultaneously is fixed at five, the scanning line density can be doubled to achieve further enhancement of the resolution.

We claim:

1. In an ultrasonic diagnostic apparatus for diagnosing the internal condition of an object medium by projecting an ultrasonic beam thereto from a vibrator array having a plurality of ultrasonic vibrators, the invention comprising:

a matrix switching circuit having vertical leadwires connected to each of said plurality of ultrasonic vibrators, delay circuit means having a plurality of individually different delays, horizontal leadwires intersecting said vertical leadwires forming a matrix, said horizontal leadwires being connected to different delays in said delay circuit means, switch control means coupled to said matrix switch circuit for sequentially connecting the intersections of said vertical and horizontal leadwires during leftward inclined and/or rightward inclining linear scanning of said vibrator array, means including said switch control means for scanning said vibrator array in a leftward-inclined linear scan which drives some of the ultrasonic vibrators at individually different times while shifting some of the vibrators sequentially to cause a sequential parallel shift of the ultrasonic beam having an angle of leftward-inclination against said vibratory array, and for scanning said vibrator array in a rightward-inclined linear scan which drives some of the ultrasonic vibrators at individually different times while sequentially shifting some of the vibrators to cause a sequential parallel shift of the ultrasonic beam having an angle of rightward-inclination against said vibrator array, means for scanning said vibrator array in a linear scan which drives some of the ultrasonic vibrators simultaneously with shifting some of the vibrators sequentially to cause a sequential parallel shift of the ultrasonic beam which is substantially perpendicular to said vibrator array, said ultrasonic vibrators which are driven at different times in said leftward-inclined linear scan and said rightward inclined linear scan being alternated between m (m=an integer) and (m+1) vibrators for finely shifting said ultrasonic beams, and means for combining the images obtained through two or more scans of said object medium to form a composite image thereof.

2. The ultrasonic diagnostic apparatus as defined in claim 1 wherein the two images obtained through the leftward-inclined and rightward-inclined linear scans of said object are combined to form a composite image.

3. The ultrasonic diagnostic apparatus as defined in claim 1 wherein each of said ultrasonic vibrators comprises a backing member and a piezoelectric vibrator plate bonded thereon which is cut into a single ultrasonic vibrator.

4. The ultrasonic diagnostic apparatus as defined in claim 3 wherein each of said ultrasonic vibrators has, on the surface thereof, a glass layer, a high polymer film and a lens layer composed of silicone rubber.

5. The ultrasonic diagnostic apparatus as defined in claim 1 wherein said means for combining said images comprises a cathode-ray tube.

6. The ultrasonic diagnostic apparatus as defined in claim 1 wherein said means for combining said images comprises a digital image memory.

7. The ultrasonic diagnostic apparatus as defined in claim 1 wherein said means for combining said images comprises a scan converter.

* * * * *